United States Patent
Xia et al.

(10) Patent No.: US 7,067,479 B2
(45) Date of Patent: Jun. 27, 2006

(54) **COMPOSITIONS WITH ENHANCED ANTIMICROBIAL EFFICACY AGAINST *E. COLI***

(75) Inventors: Erning Xia, Penfield, NY (US); Joseph C. Salamone, Fairport, NY (US); Roya Borazjani, Rochester, NY (US); Alyce K. Dobie, Williamson, NY (US); Deborah McGrath, Webster, NY (US); Zhenze Hu, Pittsford, NY (US); Daniel M. Ammon, Jr., Rochester, NY (US)

(73) Assignee: Bausch & Lomb Inc., Rochester, NY (US)

( * ) Notice: Subject to any disclaimer, the term of this patent is extended or adjusted under 35 U.S.C. 154(b) by 34 days.

(21) Appl. No.: 10/427,056

(22) Filed: Apr. 30, 2003

(65) Prior Publication Data

US 2004/0063620 A1    Apr. 1, 2004

Related U.S. Application Data

(60) Provisional application No. 60/414,957, filed on Sep. 30, 2002.

(51) Int. Cl.
  *A61K 38/16* (2006.01)
  *A61K 48/00* (2006.01)
  *A61K 31/737* (2006.01)
  *A61K 31/715* (2006.01)

(52) U.S. Cl. .............................. 514/8; 514/25; 514/54; 514/57; 510/112

(58) Field of Classification Search ................ 514/25, 514/57, 8, 54; 510/112
See application file for complete search history.

(56) References Cited

U.S. PATENT DOCUMENTS

| | | | |
|---|---|---|---|
| 4,168,112 A | 9/1979 | Ellis et al. | 351/160 H |
| 4,443,429 A | 4/1984 | Smith et al. | 424/78 |
| 4,960,799 A * | 10/1990 | Nagy | 514/567 |
| 5,382,599 A | 1/1995 | Rupp et al. | 514/547 |
| 6,274,133 B1 | 8/2001 | Hu et al. | 424/8.04 |
| 6,323,165 B1 | 11/2001 | Heiler et al. | 510/112 |

FOREIGN PATENT DOCUMENTS

| | | | |
|---|---|---|---|
| JP | 4136271 | * | 5/1992 |
| WO | WO 02/34308 A2 | | 2/2002 |
| WO | WO 02/34308 | * | 5/2002 |

OTHER PUBLICATIONS

L.H. Marsh et al., "Absorbed poly (etheyleneoxide)-poly(propyleneoxide) copolymers on synthetic surfaces: Spectroscopy and microscopy of polymer structures and effects on adhesion of skin-borne bacteria", Wiley InterScience, published Jun. 6, 2002.

* cited by examiner

*Primary Examiner*—James O. Wilson
*Assistant Examiner*—Ganapathy Krishnan
(74) *Attorney, Agent, or Firm*—Paul Lavoic

(57) ABSTRACT

Ophthalmic compositions include a polycation material to enhance antimicrobial efficacy against bacteria such as *E. coli*. The compositions include eye drop and contact lens treating solutions. A preferred polycation material is cationic cellulose derivatives.

12 Claims, No Drawings

COMPOSITIONS WITH ENHANCED ANTIMICROBIAL EFFICACY AGAINST E. COLI

FIELD OF THE INVENTION

The present invention relates to the methods and/or compositions, particularly ophthalmic compositions such as eye drop and contact lens treating solutions, with a polycation material to enhance antimicrobial efficacy against bacteria such as E. coli. Preferred polycation materials are cationic cellulose derivatives. The present invention further relates to ophthalmic compositions with lower concentrations of preservatives, yet adequate preservative efficacy, which may reduce irritation levels observed from higher concentrations of preservatives in ophthalmic compositions.

BACKGROUND

The contact of eye tissue with bacteria such as E. coli may lead to various eye infections, such as microbial keratitis. The contact of eye tissue with bacteria may result when an ophthalmic solution contaminated with bacteria is instilled directly in the eye. Examples of such ophthalmic solutions distilled directly in the eye are eye drop solutions (for example, for treating dry eye) or contact lens drop solutions (for example, for wetting a contact lens while worn). Additionally, eye tissue may be contacted with bacteria by placing a contact lens on the eye where the contact lens is contaminated with bacteria. The risk of eye infection is increased when bacteria is adhered to a contact lens, since the bacterial may remain in contact with eye tissue for a prolonged period of time.

For this reason, ophthalmic compositions, such as eye drop and contact lens treating solutions, conventionally include an antimicrobial agent which acts as a preservative, i.e., the preservative inhibits growth of bacteria, as well as other infectious organisms, in case the solution becomes contaminated with such organisms. For contact lens treating solutions, the antimicrobial agents used to preserve the solution may also serve to disinfect contact lenses when rinsed or soaked with the solution. Alternately, ophthalmic compositions may include no preservative, but in such cases, the compositions are packaged in a special container that prevents contamination of the container contents, an example being single unit-dose packages where each dosage of solution is separately packaged.

Various antimicrobial agents are known for use as preservatives in ophthalmic compositions. Such antimicrobial agents should have a broad spectrum of antimicrobial activity and be non-irritating to the eye. However, many antimicrobial agents have a tendency to irritate eye tissue, especially at higher concentrations. Therefore, it is generally advantageous to employ as low as possible concentration of antimicrobial agent to avoid the risk of eye irritation.

U.S. Pat. No. 6,323,165 to Heiler discloses compositions and methods for blocking proteinaceous deposits on hydrophilic contact lenses. The aforementioned compositions contain polyquaternium polymers that selectively bind to lenses and block such deposits.

U.S. Pat. No. 6,274,133 to Hu et al. discloses compositions for treating a silicone-hydrogel contact lens while worn in the eye. The ophthalmic solutions include a cationic cellulosic polymer that binds to the lens and prevents the accumulation of lipids, proteins and other products to the lens, especially during periods of extended wear.

U.S. Pat. No. 4,168,112 to Ellis discloses contact lens solutions especially adapted for rigid gas permeable (RGP) lenses, which contain cationic polymers that coat or form a hydrophilic polyelectrolytic complex on a lens surface. Ellis teaches an approach to solving the problem of protein deposits by trying to prevent proteins from adhering to a contact lens surface in the first place. Such a complex behaves as a hydrogel "cushion" thought to increase the wettability, hydrophilic character and/or comfort of the lens, while reducing a tendency for mucoproteins adherence to a lens surface.

U.S. Pat. No. 4,443,429 to Smith et al. discloses the use in a contact lens disinfecting solution of a dimethyldiallylammonium chloride homopolymer commercially known as Merquat™ 100 (i.e., which has a molecular weight of about 10,000 to about 1,000,000). Preferred disinfecting solution concentrations were recited therein as 0.0004 weight percent to about 0.02 weight percent (4 ppm to 200 ppm).

WO 02/34308 discloses inhibiting adhesion of bacteria to the surface of a biomedical device, such as a contact lens, by binding a cationic polysaccharide to the surface of the device.

It would be desirable to provide an ophthalmic composition with enhanced antimicrobial preservative efficacy that is safe, convenient and economical to use and non-irritating to eye tissue. The present invention is directed to overcoming the problems encountered in the art.

SUMMARY OF THE INVENTION

The present invention relates to the methods and/or compositions, such as eye drops, with a polycation material to enhance preservative efficacy against bacteria, such as E. coli. The present invention further relates to novel formulations with lower concentrations of preservatives within a wider pH range (up to 7.0), which may reduce irritation levels observed from higher concentrations of preservatives in compositions, such as eye drops.

The present invention further relates to methods and/or compositions, which includes ophthalmic solutions, which may be in the form of drops and may include a cationic cellulosic polymer that exhibits prolonged duration in the eye.

DETAILED DESCRIPTION OF THE INVENTION

As used herein, the term "ophthalmic composition" denotes a composition intended for application in the eye or intended for treating a medical device to be placed in contact with the eye such as a contact lens. Ophthalmic compositions specifically include compositions for direct instillation in the eye, including eye drop solutions such as for treating dry eye, and contact lens treating solutions distilled directly in the eye such as for rewetting a contact lens while worn. Ophthalmic compositions also include compositions instilled indirectly in the eye, such as contact lens treating solutions for treating the contact lens prior to the lens being inserted on the eye.

The term "preservative" or like terms denotes agents included in the ophthalmic compositions for the purpose of inhibiting the growth of microorganisms in the product, thereby helping to maintain sterility of the composition. The term "antimicrobial agent" denotes the specific active agent which provides the antimicrobial efficacy.

In the case of contact lens treating solutions, the methods and/or compositions of the present invention may be applicable to the conventional contact lens categories: (1) hard lenses formed from materials prepared by polymerization of acrylic esters, such as polymethyl methacrylate (PMMA), (2) rigid gas permeable (RGP) lenses formed from silicone acrylates and fluorosilicone methacrylates, (3) soft, hydrogel lenses, and (4) non-hydrogel elastomer lenses.

As an example, soft hydrogel contact lenses are made of a hydrogel polymeric material, a hydrogel being defined as a cross-linked polymeric system containing water in an equilibrium state. In general, hydrogels exhibit excellent biocompatibility properties, i.e., the property of being biologically or biochemically compatible by not producing a toxic, injurious or immunological response in a living tissue. Representative conventional hydrogel contact lens materials are made by polymerizing a monomer mixture comprising at least one hydrophilic monomer, such as (meth)acrylic acid, 2-hydroxyethyl methacrylate (HEMA), glyceryl methacrylate, N,N-dimethacrylamide, and N-vinylpyrrolidone (NVP). In the case of silicone hydrogels, the monomer mixture from which the copolymer is prepared further includes a silicone-containing monomer, in addition to the hydrophilic monomer. Generally, the monomer mixture will include a crosslinking monomer, i.e., a monomer having at least two polymerizable radicals, such as ethylene glycol dimethacrylate, tetraethylene glycol dimethacrylate, and methacryloxyethyl vinylcarbonate. Alternately, either the silicone-containing monomer or the hydrophilic monomer may function as a crosslinking agent.

In general, the present invention is directed to the compositions, such as in eye drop solutions, which may include, but are not limited to the use of polymeric compounds, antimicrobials, disinfectants and/or preservatives, etc.

The present invention relates to the methods and/or compositions, such as eye drops, with a cationic cellulose material to enhance preservative efficacy against bacteria, such as *E. coli*. The present invention further relates to novel formulations with lower concentrations of preservatives within a wider pH range (up to 7.0), which may reduce irritation levels observed from higher concentrations of preservatives in compositions, such as eye drops.

The present invention further relates to methods and/or compositions, which includes ophthalmic solutions, which may be in the form of drops and may include a cationic cellulosic polymer that exhibits prolonged duration in the eye.

The present invention may also be useful as a component of a contact lens cleaning, disinfecting or conditioning composition containing such materials. Thus, examples of material components that may be suitable and adapted for use, which are dependent upon characteristics needed for a particular application of the present invention are described below.

The compositions include a polycation material. The term "polycation" material denotes a material having multiple cationic moieties, such as quaternary ammonium radicals, in the same molecule. Many of the polycation materials, by themselves, do not have sufficient antimicrobial activity to adequately preserve an ophthalmic composition against a broad spectrum of microorganisms, but surprisingly, it has been found that the polycation material can enhance preservative efficacy against *E. coli* when used in conjunction with a conventional primary antimicrobial agent. Illustrative polycation materials include cationic polysaccharides, cationic proteins, cationic polynucleotides, cationic glycoproteins, cationic glycosaminoglycans, and ionene polymers, having multiple cationic molecules in the same molecule. It is understood that the polycation material is distinct from, and mutually exclusive of, the primary antimicrobial agent. In other words, some primary antimicrobial agents contain multiple cationic radicals; if a composition includes such a primary antimicrobial agent, then it would include an additional, separate polycation material to enhance the preservative efficacy.

In general, polyquaternium polymers suitable for use in the present invention are a well known class of polymers of which many variations are commercially available. The polyquaternium polymer, preferably includes an ophthalmologically suitable anionic organic or inorganic counterion. A preferred counterion may include, but are not limited to fluoride ions, chloride ions, bromide ions and the like.

For example, the polyquaterniums designated Polyquaternium-2 through Polyquaternium-44 (CTFA International Cosmetic Ingredient Dictionary) includes a number of materials which, based on the present teachings, are useful in the present invention. The polymerization techniques for the preparation of such materials are similarly well known to those skilled in the art and many variations of such techniques are similarly in practice in commerce.

In general, the polyquaternium polymers suitable for use in the present invention have a weight average molecular weight of about 5,000 to 5,000,000, preferably about 10,000 to 500,000, most preferably about 20,000 to 200,000. One preferred class of polycation materials is cationic polysaccharides, and especially, cationic cellulose derivatives. Specific examples include cellulosic polymers containing N,N-dimethylaminoethyl groups (either protonated or quaternized) and cellulosic polymers containing N,N-dimethylamino-2-hydroxylpropyl groups (either protonated or quaternized). Cationic cellulosic polymers are commercially available or can be prepared by methods known in the art. As an example, quaternary nitrogen-containing ethoxylated glucosides can be prepared by reacting hydroxyethyl cellulose with a trimethylammonium-substituted epoxide.

Various preferred cationic cellulosic polymers are commercially available, for example water-soluble polymers available under the CTFA (Cosmetic, Toiletry, and Fragrance Association) designation Polyquaternium-10. Such polymers are commercially available under the tradename UCARE® Polymer from Amerchol Corp., Edison, N.J., USA. These polymers contain quaternized NN-dimethylamino groups along the cellulosic polymer chain. Suitable cationic cellulosic materials have the following formula:

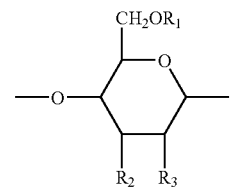

Wherein $R_1$ $R_2$ and $R_3$ are selected from H, derivatives of $C_1$-$C_{20}$ carboxylic acid, $C_1$-$C_{20}$ alkyl groups, $C_1$ to $C_3$ monohydric and dihydric alkanols, hydroxyethyl groups, hydroxypropyl groups, ethylene oxide groups, propylene oxide groups, phenyl groups, "Z" groups and combinations thereof. At least one of $R_1$ $R_2$ and $R_3$ is a Z group.

The nature of the "Z" groups is:

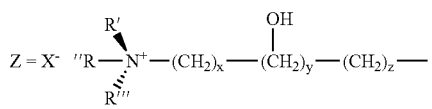

wherein: R', R" and R'" can be H, $CH_3$, $C_2H_5$, $CH_2CH_2OH$ and $CH_2CH(OH)CH_2OH$
x=0–5, y=0–4, and z=0–5
$X=Cl^-$, $Br^-$, $I^-$, $HSO_4^-$, $CHSO_4^-$, $H_2PO_4^-NO_3^-$ Various commercially available grades of the UCARE® polyquaternium-10 are summarized below:

| | JR-125 | JR-400 | JR-30 M |
|---|---|---|---|
| Brookfield Viscosity at 25° C., centipoises, 2.0% (1.7–2.2) by weight aqueous solution percent nitrogen | 110–120 cps | 400–440 cps | 12,000–13,000 cps |

In the case of eye drop solutions, the cationic polysaccharides offer the additional advantage of being effective as an active agent for treatment of dry eye. Without wishing to be bound by theory, it may be that the polymers, after binding to the mucosal tissue of the eye, in turn promote the mucin in the eye, either by supplementing the mucin and/or by helping to bind and maintain mucin on the surface of the eye. Mucins are proteins, which are heavily glycosylated with glucosamine-based moieties. Mucins have been shown to be secreted by vesicles and discharged on the surface of the conjunctival epithelium of the eye. See for example, Greiner, et al., "Mucus Secretory Vesicles in Conjunctival Epithelial Cells of Wearers of Contact Lenses," Archives of Ophthalmology, Vol. 98, pages 1843–1846 (1980). Mucins provide lubrication and additionally attract and hold moisture and sebaceous material for lubrication.

As mentioned, other polycation materials besides the cationic polysaccharides may be used in this invention. Examples include: polyquaternium-28, a polyquaternary ammonium salt based on vinylpyrrolidone and deimethylaminopropyl methacrylamide monomers (available under the tradename Gafquat HS-100, GAF Chemicals, Wayne, N.J., USA); hexadimethrine bromide, a polymer of N,N,N', N'-tetramethylhexamethylene-diamine and trimethylene bromide; hydroxypropyl guar triammonium chloride, a quaternary ammonium derivative of guar gum (available from Carbomer, Inc., Westborough, Mass., USA); copolymers of vinyl caprolactam/PVP/dimethylaminoethyl methacrylate (such as those available under the tradename Gaffix VC-713, GAF Chemicals, Wayne, N.J., USA).

Other examples are polymers containing quaternary-amine-functional repeat units, defined as repeat units each comprising a quaternary-amine group, in which a positively charged nitrogen atom is covalently bonded to four radicals (no hydrogen atoms) and ionically bonded to a negatively charged counterion such as chloride.

The term "moderately charged polyquaternium polymer" as used in the present invention, may indicate that a polymer comprise not more than about 45 mole percent net quaternary-amine-functional repeat units, wherein the mole percent net quaternary-amine-functional repeat units are the mole percent of quaternary-amine-functional (positively charged) repeat units minus the mole percent of anionic (negatively charged) repeat units in the polymer.

Suitable quaternary-amine-functional repeat units also include those found in polymeric ionenes and the like formed by a polycondensation reaction; in such repeat units, the nitrogens of the quaternary-amines are integral to the polymeric backbone and are situated between alkylene, oxyalkylene, or other segments.

Quaternary-amine-functional repeat units can also be obtained as a reaction product or two or more compounds, as for example, by the use of a strong alkylating agent such as 1,4-dichloro-2-butene which, for example, can be reacted with 1,4-bis[dimethylaminol]-2-butene and triethanolamine to produce a polymeric polyquartenary ammonium compound. Quaternary-amine-functional repeat units can also be made from other polymers, such as by the reaction of a trimethyl ammonium substituted epoxide with the hydroxy group of a hydroxyethylcellulose.

The nitrogens in the quaternary-amine-functional repeat units may be part of a saturated or unsaturated heterocyclic ring, most preferably a five- or six-membered ring. Most preferably, the polyquaternium polymer is a copolymer of a vinylimidazolium salt or a dimethyldiallyl ammonium salt. Up to 90%, preferably 40% to 90% by mole, of copolymerization-compatible comonomers not having a quaternary-amine-functionality may be copolymerized with the quaternary-amine-functional comonomers. Suitable comonomers include, but are not limited to, vinylpyrrolidone, acrylic acid, alkyl methacrylate, amides and amines such as acrylamide and N,N-dialkylaminoalkyl acrylate and methacrylate, hydroxyethylcellulose and copolymerization-compatible mixtures thereof. A preferred alkyl group has 1 to 6 carbon atoms. Most preferably, alkyl groups are methyl, ethyl, and/or butyl.

Specific polyquaternium polymers useful as a polycation material in the present invention may include, but are not limited to, copolymers in which the quaternary-amine-functional repeat units are derived from one or more of the following kinds of monomers: N,N-dimethyl-N-ethyl-aminoethyl acrylate and methacrylate, 2-methacryloxyethyltrimethylammonium, N-(3-methacrylamidopropyl)-N,N,N-trimethylammonium, 1-vinyl and 3-methyl-1-vinylimidazole, N-(3-acrylamido-3-methylbutyl)-N,N,N-trimethylammonium, N-(3-methacryloyloxy-2-hydroxypropyl)-N,N,N-trimethylammonium, diallyldimethylammonium, diallyldiethylammonium, vinylbenzyltrimethylammonium, their halides or other salt forms, and derivatives thereof, for example, involving the substitution, addition, or removal of alkyl groups, preferably having 1 to 6 carbon atoms.

A specific example of a polyquaternium copolymer is Luviquat™ FC 370 polymer (CTFA International Cosmetic Ingredient Dictionary designation polyquaternium-16 commercially available from BASF, Ludwigshafen, Germany) which is the polymerization product of a mixture of comonomers of which 70% is vinylpyrrolidone and 30% is vinylimidazolium methylchloride, commercially available as a composition with a solids content of about 40% by weight in water.

The polycation component may be employed in the compositions at about 0.001 to about 10 weight percent of the composition, preferably at about 0.005 to about 5 weight percent, with about 0.01 to about 1 weight percent being especially preferred.

As mentioned, the compositions generally include a primary antimicrobial agent. Antimicrobial agents suitable for use in the present invention include chemicals that derive their antimicrobial activity through a chemical or physiochemical interaction with the microbial organisms. These agents may be used alone or in combination.

A particularly preferred antimicrobial agent is sorbic acid (0.15%). Other known antimicrobial agents include known organic nitrogen-containing agents such as biguanides. The biguanides include the free bases or salts of alexidine, chlorhexidine, hexamethylene biguanides and their polymers, and/or combinations of the foregoing. The biguanide salts are typically gluconates, nitrates, acetates, phosphates, sulfates, halides and the like. A preferred biguanide is the hexamethylene biguanide commercially available from Zeneca, Wilmington, Del. under the trademark Cosmocil™ CQ. Generally, the hexamethylene biguanide polymers, also referred to as polyaminopropyl biguanide (PAPB), have molecular weights of up to about 100,000. Yet another example of a known primary antimicrobial agent is various materials available as polyquaternium-1.

The amount of the primary antimicrobial agent may vary depending on the specific agent employed. For the aforementioned organic nitrogen-containing agent, typically, such agents are present in concentrations ranging from about 0.00001 to about 0.5% weight percent, and more preferably, from about 0.00003% to about 0.05% weight percent. For sorbic acid, higher amounts may be required, typically 0.01 to 1 weight percent, more preferably 0.1 to 0.5 weight percent. It is preferred that the antimicrobial agent is used in an amount that will at least partially reduce the microorganism population in the formulations employed. If desired, the antimicrobial agent may be employed in a disinfecting amount, which will reduce the microbial bioburden by at least two log orders in four hours and more preferably by one log order in one hour. Most preferably, a disinfecting amount is an amount which will eliminate the microbial burden on a contact lens when used in regimen for the recommended soaking time (FDA Chemical Disinfection Efficacy Test—July, 1985 Contact Lens Solution Draft Guidelines).

The aqueous solutions employed in the present invention may contain, in addition to the active ingredients described above, one or more other components that are commonly present in ophthalmic solutions, for example, tonicity adjusting agents; buffering agents; chelating agents; pH adjusting agents, viscosity modifying agents, and demulcents and the like, which aid in making ophthalmic compositions more comfortable to the user and/or more effective for their intended use.

The aqueous solutions of the present invention are typically adjusted with tonicity agents to approximate the tonicity of normal lacrimal fluids (approximately equivalent to a 0.9% solution of sodium chloride or 2.8% glycerol solution). The solutions are made substantially isotonic with physiological saline used alone or in combination with other adjusting agents. The ophthalmic compositions preferably have an osmolality of about 225 mOsm/kg to 400 mOsm/kg, more preferably 280 mOsm/kg to 320 mOsm/kg.

The compositions may include chelating or sequestering agents in order to chelate or bind metal ions, which might otherwise react with the lens and/or protein deposits and collect on the lens. Examples of such preferred materials, may include, but are not limited to ethylene-diaminetetraacetic acid (EDTA) and its salts (disodium), which are usually added in amounts ranging from about 0.01 weight percent to about 0.2 weight percent.

Compositions, such as aqueous solutions, for use in the present invention, may be formulated as lens conditioning solutions or eye-drops and sold in a wide range of small-volume containers from 1 ml to 30 ml in size. Such containers can be made from HDPE (high density polyethylene), LDPE (low density polyethylene), polypropylene, poly(ethylene terepthalate) and the like. For eye drops, flexible bottles having conventional dispensing tops are especially suitable for use with the present invention. The eye-drop formulation of the invention is used by instilling, for example, about one (1) or three (3) drops in the eye(s) as needed.

The pH of the solutions and/or compositions of the present invention may be maintained within the range of pH=5.0 to 8.0, preferably about pH=6.0 to 8.0, more preferably about pH=6.5 to 7.8, most preferably pH values of greater than or equal to 7; suitable buffers may be added, such as borate, citrate, bicarbonate, tris(hydroxymethyl) aminomethane (TRIS-Base) and various mixed phosphate buffers (which may include combinations of $Na_2HPO_4$, $NaH_2PO_4$ and $KH_2PO_4$) and mixtures thereof. Borate buffers are preferred when the primary antimicrobial agent is PAPB. Generally, buffers will be used in amounts ranging from about 0.05 percent by weight to 2.5 percent by weight, and preferably, from 0.1 percent by weight to 1.5 percent weight.

The compositions of this invention can be prepared by a variety of techniques conventionally used in the art. One method involves a two-phase compounding procedures. In the first phase, about 30 percent of the distilled water is used to dissolve the polymeric components (such as the cationic cellulosic polymer) with mixing for about 30 minutes at around 50° C. The first-phase solution is then autoclaved at about 120° C. for 30 minutes. In a second phase, other components, such as alkali metal chlorides, sequestering agents, preservatives and buffering agents, are then dissolved in about 60 percent of the distilled water with agitation, followed by adding the balance of distilled water. The second-phase solution can then be sterilely added into the first-phase solution by forcing it through an 0.22 micron filter by means of pressure, followed by packaging in sterilized plastic containers.

The materials suitable for use in the present invention may also be useful as a component of a cleaning, disinfecting or conditioning solution and/or composition. Such solutions and/or compositions also may include, antimicrobial agents, surfactants, toxicity adjusting agents, buffers and the like that are known to be used components of conditioning and/or cleaning solutions for contact lenses. Examples of suitable formulations for cleaning and/or disinfecting solutions are taught in U.S. Pat. No. 5,858,937 to Richard et al., which is incorporated by reference as if set forth at length herein. Preferably, compositions and/or solutions of the present invention may be formulated as a "multi-purpose solution," meaning that such compositions and/or solutions may be used for cleaning, chemical disinfection, storing, and rinsing a contact lens. A multi-purpose solution preferably has a viscosity of less than 75 cps, preferably 1 to 50 cps, and most preferably 1 to 25 cps and is preferably is at least 95 percent weight by volume water in the total composition.

Surfactants, which are suitable for use in the present invention, are classified into cationic surfactants, anionic surfactants, nonionic surfactants and ampholytic surfactants depending upon their dissociation state in their aqueous solutions. Among them, various surfactants which are classified into cationic surfactants, particularly surfactants which consist of an amino acid derivative, i.e. amino acid type cationic surfactants, have conventionally been proposed as disinfectant cleaning agents or compositions for disinfection. Glycerin may also be included as a component of the present invention. Amphoteric surfactants suitable for use in a composition according to the present invention include materials of the type are offered commercially under the trade name "Miranol." Another useful class of amphoteric surfactants is exemplified by cocoamidopropyl betaine, commercially available from various sources.

Various other surfactants suitable for use in the composition can be readily ascertained, in view of the foregoing description, from McCutcheon's Detergents and Emulsifiers, North American Edition, McCutcheon Division, MC Publishing Co., Glen Rock, N.J. 07452 and the CTFA International Cosmetic Ingredient Handbook, Published by The Cosmetic, Toiletry, and Fragrance Association, Washington, D.C.

Optionally, one or more additional polymeric or non-polymeric demulcents may be combined with the above-named ingredients. Demulcents are known to provide wetting, moisturizing and/or lubricating effects, resulting in increased comfort. Polymeric demulcents can also act as a water-soluble viscosity builder. Included among the water-soluble viscosity builders are the non-ionic cellulosic polymers like methyl cellulose, hydroxyethyl cellulose, hydroxypropyl cellulose, and carboxymethyl cellulose, poly(N-vinylpyrrolidone), poly(vinylalcohol) and the like. Such viscosity builders or demulcents may be employed in a total amount ranging from about 0.01 to about 5.0 weight percent or less. Suitably, the viscosity of the final formulation is 10 cps to 50 cps. Comfort agents such as glycerin or propylene glycol can also be added.

EXAMPLES

The following general procedure was used for evaluating the efficacy of various eye drop solutions against *E. coli* ATCC 8739, as well as various other pathogenic organisms. This procedure applies to the FDA premarket notification (510(k)) guidance document and ISO/DIS 14730 standard preservative efficacy testing with a 14 day rechallenge. The evaluations were conducted with 3 separate lots of product. Each lot was tested with a different preparation of *E. coli*.

Cells of *E. coli* ATCC 8739 were grown on Tryptic Soy Agar (TSA) slants at 30–35° C. in an incubator for 18 to 24 h. Cells were harvested in 5–10 ml of Saline TS (USP, 0.9% saline)) which was added to each agar slant, followed by gentle agitation with a sterile cotton swab. The cell suspensions were aseptically dispensed into separate sterile polypropylene centrifuge tubes. Cells were harvested by centrifugation at 3000 rpm for 10 min, washed one time and suspended in Saline TS to a concentration of about 2×10⁸ cells per ml.

The cell suspension (0.1 ml) was diluted with 20 ml of the article (test solution) to reach a final concentration of $1.0 \times 10^5$–$1.0 \times 10^6$ colony forming units (CFU). Phosphate Buffered Saline (PBS) was used as a control article. The inoculated test and control articles were incubated at 20–25° C. in static culture. At time zero, 1 ml of the PB (Phosphate Buffer, USP, pH 7.2) from the control article was diluted with 9 ml of PB and serially diluted cells were plated in triplicate on TSA. The plates were incubated at 30–35° C. for 2–4 days.

Similarly, at days 7 and 14, a 1 ml volume from test articles was added into 9 ml of Dey-Engley neutralizing broth (DEB) and serially diluted in DEB and plated in triplicate on TSA. Plates were incubated at 30–35° C. for 2–4 days and developing colonies counted.

Immediately following the day 14 sampling, test articles were re-inoculated to give final concentrations of $1.0 \times 10^4$–$1.0 \times 10^5$ of *E. coli*. At time zero, 1 ml from the inoculum control was added to 9 ml of PB and subsequent serial dilutions were plated in triplicate on TSA. Plates were incubated at 30–35° C. for 2–4 days.

At days 21 and 28, 1 ml from the test articles was added to 9 ml of Dey-Engley neutralizing broth (DEB) and again, serial dilutions were plated in triplicate on TSA. Plates were incubated at 30–35° C. for 2–4 days and developing colonies counted.

Based on the acceptance criteria for bacteria (*E. coli*) a solution is acceptable if the number of viable bacteria recovered per ml is reduced by at least 3.0 logs at day 14 and after the rechallenge at day 14, the concentration of bacteria is reduced by at least 3.0 logs by day 28.

The results at day 14 and 28 days for the tested solutions are shown in the following tables, where "ND" denotes "no detectable bacterial levels".

TABLE 1

| Ingredient (W/W %) | | Example 1 | Comparative Example 1 |
| --- | --- | --- | --- |
| Tris-Base | | 0.1210 | 0.1210 |
| Sodium Borate | | 0.2198 | 0.2198 |
| Glycerin | | 1.0000 | 1.0000 |
| Sodium Chloride | | 0.2660 | 0.2660 |
| Poloxamine 1107 | | 1.0000 | 1.0000 |
| Poloxamer F127 | | 2.0000 | 2.0000 |
| Cationic cellulose polymer (Polyquaternium-10 - UCARE Polymer JR) | | 0.0200 | — |
| Sorbic Acid | | 0.2000 | 0.2000 |
| EDTA | | 0.2000 | 0.2000 |
| Preservative Efficacy (ISO) | | Passed | Failed |
| *S. aureus* | 14 | >4.7 | >4.7 |
| | 28 | >3.7 | ND |
| *P. aeruginosa* | 14 | >4.6 | >4.6 |
| | 28 | >3.6 | ND |
| *E. coli* | 14 | >4.6 | 1.9 |
| | 28 | >3.6 | ND |
| *C. albicans* | 14 | 0.3 | 0.4 |
| | 28 | 0.4 | ND |
| *A. niger* | 14 | 0.8 | 0.7 |
| | 28 | −0.1 | ND |

TABLE 2

| Ingredient (W/W %) | Example 2 | Comparative Example 2 |
| --- | --- | --- |
| Tris-Base | 0.1210 | 0.1210 |
| Sodium Borate | 0.2198 | 0.2198 |
| Glycerin | 1.0000 | 1.0000 |
| Sodium Chloride | 0.2660 | 0.2660 |
| Poloxamine 1107 | 1.0000 | 1.0000 |
| Poloxamer F127 | 2.0000 | 2.0000 |
| Cationic cellulose polymer (Polyquaternium-10 - UCARE Polymer JR) | 0.0200 | — |
| Sorbic Acid | 0.1650 | 0.1650 |
| EDTA | 0.2000 | 0.2000 |
| | | ND |
| Preservative Efficacy (ISO) | Passed | Failed |
| *S. aureus* 14 | >4.7 | 3.2 |
| 28 | | ND |
| *P. aeruginosa* 14 | >4.6 | >4.6 |
| 28 | | ND |
| *E. Coli* 14 | >4.5 | 2.6 |
| 28 | | ND |
| *C. albicans* 14 | 0.5 | 0.4 |
| 28 | | ND |
| *A. niger* 14 | 0.4 | 0.5 |
| 28 | | ND |

TABLE 3

| Ingredient (W/W %) | Example 3 | Comparative Example 3 |
|---|---|---|
| Tris-Base | 0.1210 | 0.1210 |
| Sodium Borate | 0.2198 | 0.2198 |
| Glycerin | 1.0000 | 1.0000 |
| Sodium Chloride | 0.2660 | 0.2660 |
| Poloxamine 1107 | 1.0000 | 1.0000 |
| Poloxamer F127 | 2.0000 | 2.0000 |
| Cationic cellulose polymer (Polyquaternium-10 - UCARE Polymer JR) | 0.0200 | — |
| Sorbic Acid | 0.1650 | 0.1650 |
| EDTA | 0.1750 | 0.1750 |
| | | ND |
| Preservative Efficacy (ISO) | Passed | Failed |
| S. aureus 14 | 4.0 | 3.8 |
| 28 | | ND |
| P. aeruginosa 14 | >4.6 | >4.6 |
| 28 | | ND |
| E. Coli 14 | >3.8 | 1.8 |
| 28 | | ND |
| C. albicans 14 | 0.6 | 0.5 |
| 28 | | ND |
| A. niger 14 | 0.6 | 0.5 |
| 28 | | ND |

TABLE 4

| Ingredient (W/W %) | Example 4 | Comparative Example 4 |
|---|---|---|
| Tris-Base | 0.1210 | 0.1210 |
| Sodium Borate | 0.2198 | 0.2198 |
| Glycerin | 1.0000 | 1.0000 |
| Sodium Chloride | 0.2660 | 0.2660 |
| Poloxamine 1107 | 1.0000 | 1.0000 |
| Poloxamer F127 | 2.0000 | 2.0000 |
| Cationic cellulose polymer (Polyquaternium-10 - UCARE Polymer JR) | 0.0200 | — |
| Sorbic Acid | 0.2000 | 0.2000 |
| EDTA | 0.1750 | 0.1750 |
| | pH = 6.80 | pH = 6.8 |
| Preservative Efficacy (ISO) | Passed | Failed |
| S. aureus 14 | >4.7 | 3.6 |
| 28 | | ND |
| P. aeruginosa 14 | >4.6 | >4.6 |
| 28 | | ND |
| E. Coli 14 | 3.4 | 2.2 |
| 28 | | ND |
| C. albicans 14 | 0.5 | 0.4 |
| 28 | | ND |
| A. niger 14 | 0.3 | 0.5 |
| 28 | | ND |

TABLE 5

| Ingredient (W/W %) | Example 5 | Comparative Example 5 |
|---|---|---|
| Tris-Base | 0.1210 | 0.1210 |
| Sodium Borate | 0.2198 | 0.2198 |
| Glycerin | 1.0000 | 1.0000 |
| Sodium Chloride | 0.2660 | 0.2660 |
| Poloxamine 1107 | 1.0000 | 1.0000 |
| Poloxamer F127 | 2.0000 | 2.0000 |
| Cationic cellulose polymer (Polyquaternium-10 - UCARE Polymer JR) | 0.0200 | — |
| Sorbic Acid | 0.2000 | 0.2000 |
| EDTA | 0.2000 | 0.2000 |
| | pH = 7.0 | pH = 7.0 |
| Preservative Efficacy (ISO) | Passed | Failed |
| S. aureus 14 | >4.7 | 3.3 |
| 28 | | ND |
| P. aeruginosa 14 | >4.6 | >4.6 |
| 28 | | ND |
| E. Coli 14 | 4.0 | 1.9 |
| 28 | | ND |
| C. albicans 14 | 0.5 | 0.5 |
| 28 | | ND |
| A. niger 14 | 0.3 | 0.5 |
| 28 | | ND |

The addition of low concentration (0.01–0.5%) of a cationic cellulose (such as polymer JR materials) reacting in a synergistic effect with other components, such as sorbic acid and EDTA may affect the state of the microorganism cell surface and enhance the binding affinity of preservatives on a cell wall. Moreover, the presence of Polymer JR materials in the present invention showed a significantly improved preservative efficacy against E. Coil without significantly increasing the combined concentration of sorbic acid and EDTA. The present invention further provides a new broader-spectrum and more efficacious preservative system in the eye care products market.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method for enhancing antimicrobial efficacy of a composition against E. coli comprising including a polyquaternium-10 cationic cellulosic polymer in said composition containing a primary antimicrobial agent.

2. The method according to claim 1, wherein the cationic cellulosic polymer is included in said composition in an amount ranging from about 0.001 to about 0.5 weight percent.

3. The method according to claim 1, wherein the composition is an ophthalmic solution.

4. The method according to claim 1, wherein the composition is an aqueous solution that further comprises at least one component selected from the group consisting of tonicity adjusting agents, buffering agents, chelating agents, and viscosity modifying agents.

5. The method according to claim 1, wherein the primary antimicrobial agent includes sorbic acid.

6. The method according to claim 1, wherein the primary antimicrobial agent includes a biguanide.

7. An ophthalmic composition comprising a primary antimicrobial agent, and a polyquaternium-10 cationic cellulosic polymer in an aqueous solution, wherein said cationic cellulosic polymer enhances the antimicrobial efficacy of the primary antimicrobial agent.

8. The ophthalmic composition according to claim 7, wherein the composition further comprises at least one component selected from the group consisting of tonicity adjusting agents, buffering agents, chelating agents, and viscosity modifying agents.

9. The ophthalmic composition according to claim 7, having the form of an eye drop solution.

10. The ophthalmic composition according to claim 7, having the form of a contact lens treating solution.

11. The ophthalmic composition according to claim 9, being suitable for direct instillation in the eye without irritation to eye tissue.

12. An ophthalmic composition comprising a primary antimicrobial agent and a polyquaternium-10 cationic cellulosic polymer that enhances the antimicrobial efficacy of said primary antimicrobial agent, wherein said composition adequately preserves said composition against *E. coli*, whereas a similar composition lacking the polyquaternium-10 cationic cellulosic polymer does not adequately preserve said similar composition against *E. coli*.

* * * * *